United States Patent [19]

Nielsen et al.

[11] Patent Number: 4,465,063
[45] Date of Patent: Aug. 14, 1984

[54] CARDIAC FLOW MEASUREMENT SYSTEM AND METHOD

[75] Inventors: Steven D. Nielsen, Sandy, Utah; Peter Willshaw, Buenos Aires, Argentina

[73] Assignee: University of Utah, Salt Lake City, Utah

[21] Appl. No.: 381,965

[22] Filed: May 25, 1982

[51] Int. Cl.³ .............................................. A61B 5/02
[52] U.S. Cl. .................................... 128/1 D; 128/713
[58] Field of Search ................ 128/713, 748, 691, 1 D

[56] References Cited

U.S. PATENT DOCUMENTS 3,376,660 4/1968 McGinnis ........................ 128/1 D X
3,718,044 2/1973 Joyce, Jr. et al. .................... 73/223

FOREIGN PATENT DOCUMENTS

2658104 12/1977 Fed. Rep. of Germany .
2004942 4/1979 United Kingdom .
733688 5/1980 U.S.S.R. .

Primary Examiner—Lee S. Cohen
Assistant Examiner—Angela D. Sykes
Attorney, Agent, or Firm—Workman, Nydegger & Jensen

[57] ABSTRACT

The volume of blood pumped by an artificial ventricle or ventricular assist device is extracorporeally monitored as a function of the volume of fluid used to drive the ventricle. The ventricle is divided into two chambers by a flexible diaphragm. Fluid is alternately supplied to one chamber during systole and then removed from that chamber during diastole. In the preferred embodiment, during systole the rate of fluid flow is sensed by establishing a differential pressure between two points in the fluid's flow path. The differential pressure is converted to a proportional voltage which may be integrated to provide the desired volume over a given time interval, which corresponds to the cardiac output within ±5-10%.

27 Claims, 5 Drawing Figures

CARDIAC FLOW MEASUREMENT SYSTEM AND METHOD

BACKGROUND OF THE INVENTION

1. Field of the Invention

The present invention relates to systems and methods for providing cardiac flow measurement and, more particularly, to a system and method for providing measurement of the volume of blood pumped by an artificial heart.

2. The Prior Art

In the human circulatory system, blood is first pumped through the lungs, where oxygen and carbon dioxide are exchanged. It then returns to the heart and is pumped out into the systemic circulatory vessels. The blood leaves the heart through the aorta, which is typically 25 millimeters in diameter, and then flows on through progressively narrowing vessels until it reaches the capillaries, which are some eight micrometers in diameter. The blood then flows through progressively larger vessels as it moves through the venous system, until it reaches the vena cava, where the vessel diameter is about 20 millimeters. The velocities that are encountered in the human circulatory system vary between 1 m/sec in the larger vessels to $10^{-4}$ m/sec in the capillaries. Pressures may vary between 150 mm of Hg in the aorta to nearly zero in the major veins.

The prime mover in the human circulatory system is the heart. In a normal adult at rest, the heart has an output of about 5,000 ml/minute at a mean rate of about 70 beats per minute. During periods of exercise, this output can rise by a factor of five. Assuming a classical lifespan of about 70 years, before the end of its useful life a normal heart will have pumped approximately 200,000 tons of blood through the circulatory system, normally without maintenance.

With recent advances in technology and medical procedures, it is now possible to treat critically ill heart patients in some cases by total replacement of a defective heart with a normal heart from a human donor. Such heart transplants are now well known and have received widespread attention. However, obviously the number of donors who can provide a normal heart for replacement of a defective one in a critically ill patient is extremely limited. This suggests the importance of developing a totally artificial heart for replacement of the natural heart in such patients.

Investigation into the development of an artificial heart that can be satisfactorily transplanted in critically ill patients has been the subject of intensive research in recent years. Efforts in this area are beginning to culminate, with the hope that before long critically ill heart patients will have a chance to enjoy prolonged life by means of an artificial heart transplant.

One of the more promising types of artificial hearts which has been developed consists of an artificial ventricle having a base on which is mounted a semi-rigid urethane polymer chamber which contains prosthetic heart valves to regulate the entry and exit of blood. The blood chamber and base are separated by a flexible diaphragm. The pumping action of the artificial ventricle is controlled by a "heart driver." The function of the heart driver is to impart a pumping action to the flexible diaphragm. This may be done mechanically, hydraulically or pneumatically. For example, in one type of pneumatic unit the heart driver is connected to the base of the ventricle by a flexible plastic tube known as the "driver tube." The driver tube is in turn connected at its origin to the outlet to an electropneumatic valve. The heart driver controls the valve so as to alternately connect the driver tubing to a source of compressed air during systole (i.e., during the phase of the heart's operation where blood is expelled from the heart) and to an exhaust port during diastole (i.e., that phase of the heart's operation where the heart is relaxed and the blood re-enters the heart chambers).

During systole, compressed air is allowed to enter the gas chamber of the ventricle and in so doing exerts a force on the blood contained in the blood chamber of the ventricle via the flexible diaphragm. This force is sufficient to cause the flexible diaphragm to expel the blood through the outflow valve. The duration of the systolic phase of operation is electronically controlled and ends by de-actuation of the electropneumatic valve which then transfers the driver tubing connection from the compressed air source to the exhaust port. This releases the pressure on the flexible diaphragm so that blood can then re-fill the ventricle via the inflow valve.

Recent studies in which either fluid (i.e., pneumatically or hydraulically) driven or mechanically driven types of artificial hearts have been transplanted in animals have yielded promising results, and efforts are now underway to begin limited experimental use of these types of artificial hearts in human patients.

In the past, one of the difficulties arising out of the use of heart replacement with a fluid or mechanically driven artificial heart has been the difficulty of obtaining reliable direct measurements of hemodynamic parameters like pressures, venous return and cardiac output. Knowledge of the cardiac output is useful in monitoring the circulation of a critically ill patient, especially if repeated information can be obtained speedily and easily and with the least possible interference with treatment and recovery of the patient. Especially after total heart replacement, the continuous and reliable measurement of these parameters is the basis for determining whether the artificial heart is properly functioning. It is also the basis for providing automatic control of the heart driver.

There have been several methods and systems employed to measure cardiac output in the prior art; however, all of these have been less accurate than desirable and they also have severe practical problems or risks associated with their use, which in almost every case requires some type of invasive technique.

For example, one widely known method for measuring cardiac output is called the Fick technique, which is performed by measuring the oxygen consumed by the patient by means of a specialized apparatus. Catheters are employed to withdraw venous blood at the right ventricle and arterial blood from the carotid artery. The difference in oxygen content between arterial and venous blood for any given oxygen consumption is an index of cardiac output, which may be calculated from these measured variables.

The Fick method is rather laborious, has an undesirable aspect of requiring insertion of arterial and venous catheters as well as collection of expired gas, and has a measurement accuracy that is only in the range of ±10–20% of the actual cardiac output.

Another prior art method for providing flow measurement is called the dye-dilution method. This method involves injecting dye into the blood stream at a point upstream of the ventricle and then sampling the blood downstream of the ventricle. The concentration of dye measured per unit of time in the blood downstream of the ventricle provides an indication of the cardiac output.

Like the Fick technique, the dye-dilution method also suffers from a relatively poor measurement accuracy, in the range of ±10–20% of the true value. Moreover, when used with an artificial heart the dye-dilution technique creates an additional problem by virtue of the fact that an artificial heart valve will not fully close when a catheter is threaded through the valve, which is necessary to inject the dye. Therefore, the artificial valve leaks considerably and it is not possible to provide a true and accurate measurement of cardiac flow under these circumstances.

Yet another prior art method is the thermal-dilution technique, which is described in an article entitled "Cardiac Output Measurement By Thermal-Dilution" by Sorenson et al. See *Annals of Surgery*, Vol. 183, No. 1, January 1976, pp. 67–72. This technique involves placing a catheter via a vein so that its tip passes through the right ventricle to lie in the pulmonary artery. A thermistor is located near the catheter tip. Cool saline solution is delivered into the upper end of the catheter, to emerge in the right ventricle and temperature measurements from the thermistor, at the downstream location, are measured over a given time interval and can be used to provide an estimate of cardiac output.

One problem with the thermal-dilution technique is the fact that changes in temperature of the saline solution occurring between its introduction point and measurement point render accurate detection and other measurement difficult. The technique has an accuracy of only ±20% of the actual flow value. Moreover, the thermal-dilution technique suffers from the same problem as the dye-dilution technique when used with an artificial heart, in that an artificial heart valve will not fully close when a catheter is threaded through it to introduce the saline solution into the patient's circulatory system.

Still another prior art method for measuring cardiac output is described in an article entitled "The Measurement of Flow in Intact Blood Vessels" by Roberts. See *CRC Critical Reviews in Bioengineering*, August 1973, pp. 419–452. Basically, this technique involves the use of an electromagnetic flow meter. The electromagnetic flow meter exploits the fact that a moving electrical conductor generates a voltage when it passes through a magnetic field. In the case of this type of flow meter, the blood acts as the moving conductor. A coil of wire around the blood vessel is used to generate the magnetic field and electrodes applied to the blood vessel are used to detect the voltage generated by the moving blood.

This device works particularly well on a laboratory bench, but experiences serious difficulties when employed in vivo. For example, the electrodes must be firmly applied to the vessel wall; however, any movement of the body can adversely affect this arrangement. The wires connected to the electrodes and coil are fragile, and major surgery is required to put the device into the patient's body. Moreover, once the device is in the patient's body, it cannot be calibrated.

In summary, the prior art systems for providing cardiac flow measurement do not provide the necessary degree of accuracy to be able to provide reliable data which can be used in diagnosing whether an artificial heart is properly functioning or which can be reliably used as the basis for controlling the heart driver. Moreover, as indicated, these prior art techniques have the further serious drawback that they involve invasive techniques which pose additional risk and discomfort to the patient, which is undesirable, particularly in the case of a critically ill cardiac patient.

SUMMARY AND OBJECTS OF THE INVENTION

It is an object of the present invention to provide an improved system and method for providing reliable, accurate flow measurements for a fluid driven or mechanically driven artificial ventricle.

It is another object of the present invention to provide a system and method for providing accurate flow measurements of an artificial ventricle without having to require invasive placement of catheters and the like in the body of a patient.

It is still another object of the present invention to provide a system and method for measuring ventricular output which is both simple to use and compact and economical in its construction.

In accordance with the foregoing objects of the present invention, in one presently preferred embodiment pressurized gas is applied during systole through a driver tube to the gas chamber of a ventricle of a pneumatically driven artificial heart and is exhausted therefrom during diastole. The gas chamber is separated from the ventricle blood chamber by a flexible diaphragm which mechanically transmits pressure but not flow between the gas and blood chambers. During diastole, when the gas chamber pressure falls below aortic pressure, there is a reflux of blood from the aorta to the ventricle blood chamber which results in the closure of the outflow valve. When the gas chamber pressure falls below atrial pressure, the inflow valve of the blood chamber opens and blood enters the ventricle. The volume of blood entering the blood chamber during diastole is matched by an equivalent volume of gas exhausted from the gas chamber. The pressure in the gas exhaust path is essentially constant and quite close to ambient during this phase. Therefore, the volume of blood entering the ventricle during diastole can be measured as a function of the volume of air exhausted during diastole, which can easily be derived by measuring the rate of air flow and then integrating. Similarly, even though the pressure in the driver tube changes quite rapidly over a wide range of values during systole, the volume of blood expelled from the ventricle during systole can be measured as a function of the volume of pressurized air applied to the gas chamber of the ventricle if a flow meter is used that measures rate of air flow independently of the air pressure.

In the preferred embodiment of the invention, the volume of air applied to the gas chamber of the ventricle during systole is measured by measuring the rate of air flow through the driver tube independently of pressure and then integrating this flow rate with respect to time to derive the volume. To achieve this, a pneumotachograph is inserted in the driver tube to provide a differential pressure which is proportional to the flow rate but which is insensitive to absolute pressure changes occurring therein. The differential pressure is converted to a proportional analog voltage which is digitized by sampling the analog signal. The digitized data is then input to a digital computer where it is stored. The computer then performs the required integration. The output is then displayed both graphically and numerically on a terminal system.

The method and apparatus of the present invention is relatively compact and simple to use, yet it provides measurement accuracies of within ±5-10% of actual ventricular output. Moreover, the technique is noninvasive, and thus does not cause additional risk, pain or discomfort to the patient, and yet aids the patient's treatment and recovery. In addition to the measurement of ventricular output, the display of the air flow time curve contains information concerning the functional characteristics of the valves and ventricle. This information can provide early warning of ventricular malfunction or dangerous hemodynamic states, enabling corrective action to be taken before the patient is seriously endangered.

The foregoing objects and other features of the present invention will become more fully apparent from the following description and appended claims taken in conjunction with the accompanying drawings.

DETAILED DESCRIPTION OF THE PREFERRED EMBODIMENTS

Figure 1:
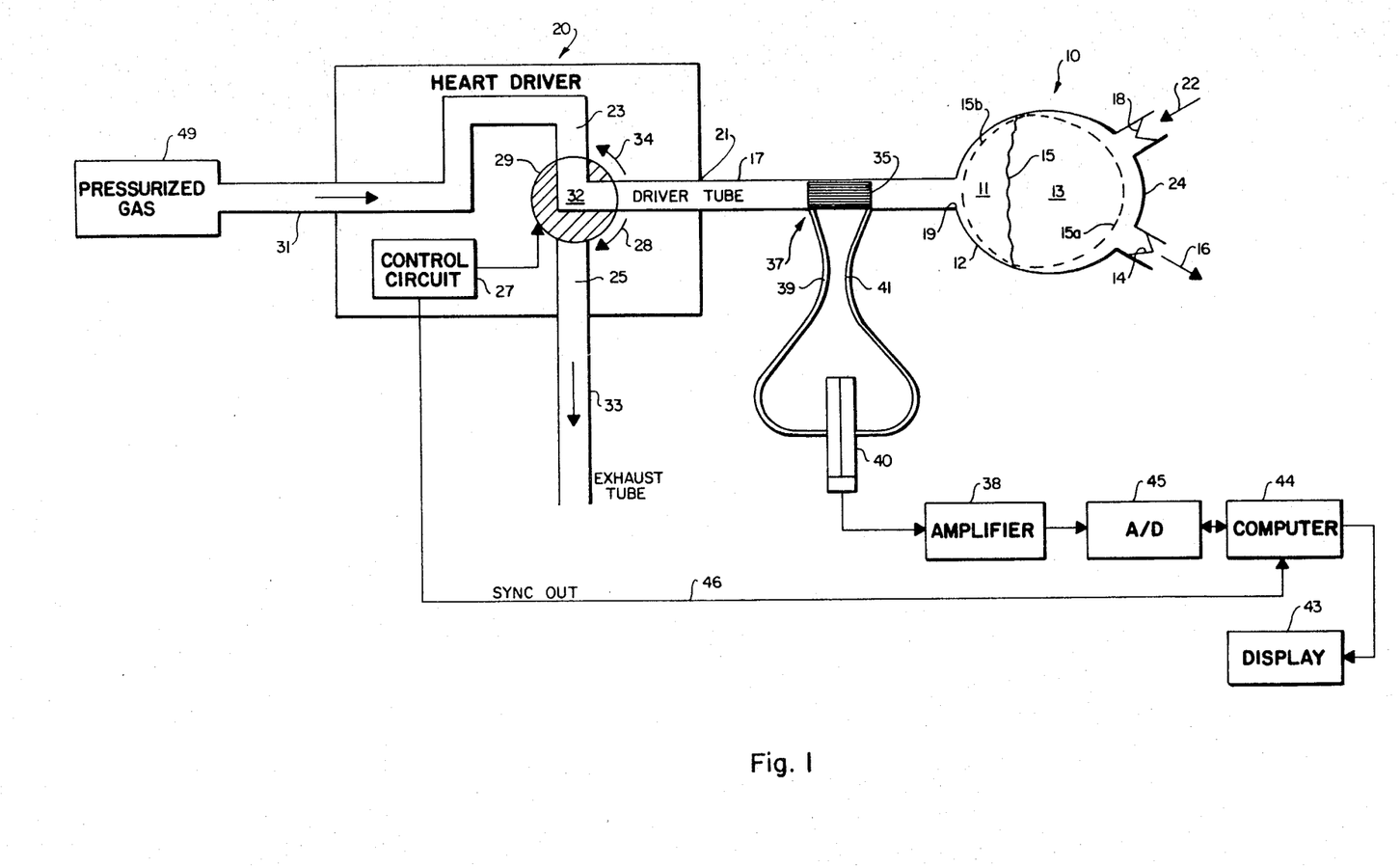
FIG. 1 is a schematic representation of one presently preferred embodiment of the system and method of the present invention wherein ventricular blood flow measurements are derived from the rate of air flow to the artificial ventricle during systole or diastole.

Referring specifically to FIG. 1 of the accompanying drawings, an artificial ventricle is generally illustrated at 10. The artificial ventricle may be either a left or a right ventricle or ventricular assist device that is either implanted in the patient or that is located extracorporeally. The ventricle 10 is separated into two chambers 11 and 13 by a flexible diaphragm 15. As hereinafter more fully described, a pumping action may be imparted to the flexible diaphragm 15 by means of a drive fluid that alternately enters into and then leaves chamber 11, or by means of a direct mechanical coupling to a piston or other similar mechanical device. In the case of a fluid driven system, the drive fluid may be gaseous (ie., a pneumatic system) or liquid (i.e., a a hydraulic system). Thus, as used herein, the term "fluid" is intended to mean either a gaseous or a liquid drive fluid.

For purposes of the embodiment specifically illustrated in FIG. 1, ventricle 10 may be part of any pneumatically driven artificial heart or ventricular assist device and, for example, may be part of the Jarvik 7 Implantable Total Artificial Heart sold by Kolff Medical, of Salt Lake City, Utah. The two chambers 11 and 13 are separated by a flexible diaphragm 15 which is impervious to flow of gas or blood, but which transmits pressure differences between the chambers by flexing and thereby differentially varying the chamber volumes. For example, as hereinafter more fully described, during systole the diaphragm is caused to flex by a pressurized gas so that it moves to a position such as illustrated by the dashed line configuration 15a. In this configuration the diaphragm exerts a force on the blood in chamber 13, expelling it through an outflow valve 14, as schematically represented by arrow 16. During diastole, the pressurized gas is released or removed from chamber 11. Blood then re-enters chamber 13 through inflow valve 18, as schematically represented by arrow 22, and displaces the diaphragm to a position such as that illustrated at 15b.

The ventricle 10 is typically made of an aluminum base 12 on which is mounted a semi-rigid urethane polymer shell 24 which contains the prosthetic heart valves 14, 18 which regulate the ingress and egress of blood. The pressurized gas chamber 11 is connected to a driver tube 17 which conducts pressurized gas into and out from the gas chamber 11. It should be noted that separate tubes and separate openings may be provided, if desired, for inlet and outlet of the gas. Typically, although not shown in the schematic representation of FIG. 1, the base 12 is fitted with a tubular connector for connection to driver tube 17 at the ingress/egress port 19 of ventricle 10.

The other end of driver tube 17 is connected through a port 21 of a heart driver unit 20 to an electropneumatically controlled valve 29. The heart driver 20 which is illustrated schematically in FIG. 1, is electrically controlled by circuit 27 so that it alternately connects the valve 29 to a systole (or supply) port 23 and a diastole (or exhaust) port 25. For example, as illustrated in FIG. 1, valve 29 is connected so that it will conduct the pressurized gas from container 49 through a supply tube 31, elbow-shaped passageway 32 of valve 29, and to driver tube 17. If the valve 29 is rotated 90° clockwise, as schematically represented by arrow 28, the elbow-shaped passageway 32 will complete the flow path between the driver tube 17 and exhaust tube 33, thus permitting the gas to be exhausted to atmosphere during diastole. Thus, by alternately rotating the valve 90° clockwise and then 90° counterclockwise as represented by arrows 28 and 34, the pressurized gas can be admitted to gas chamber 11 and then exhausted therefrom so as to cause the pumping action of diaphragm 15.

It is to be understood that the heart driver 20, with valve 29 and the associated control circuit 27 are shown in FIG. 1 by way of schematic illustration only. The actual mechanism for valve 29 may be any suitable three-port solenoid valve or combination of solenoid valves. An example of a commercially available unit which can serve as the heart driver 20, including valve 29 and control circuit 27, is the Utah Heart Driver sold by Kolff Medical, of Salt Lake City, Utah, which is described and illustrated in detail in the Utah Heart Driver—Operations, Specifications, and Parts Manual, dated February, 1981. The cardiac frequency, as controlled by this heart driver, it operator-adjustable by means of circuit 27.

As indicated above, while FIG. 1 specifically illustrates one presently preferred embodiment which includes a single pass pneumatically driven ventricle, other drive systems could be used equally well. For example, the system could be hydraulic or pneumatic, and the drive fluid (either liquid or gas) could be recycled (i.e., a "multi-pass" system) rather than exhausted from the system with each cycle as in the case of a single pass system. The drive system could also be mechanical, in which case a piston or other similar device would be used to drive the diaphragm 15 rather than a fluid. In the case of a mechanically driven system, the fluid admitted and expelled from chamber 11 during each cycle is passive—that is, does no work in terms of pumping diaphragm 15, and is used to simply fill the available space in chamber 11. Mechanical, hydraulic or pneumatic drive systems such as those described herein are well-known and are commercially available.

In the embodiment illustrated in FIG. 1, a flow meter 37 is placed in the flow path of driver tube 17 at a point that is outside of the patient's body. In the presently preferred embodiment, flow meter 37 takes the form of a pneumotachograph, such as the Fleisch pneumotachograph Model i/a 7318 sold by OEM Medical, Inc., of Richmond, Va. However, for this embodiment of the invention any flow meter which is insensitive to the rapidly changing pressures developed by the air flow through driver tube 17 during systole or diastole could be used in place of the pneumotachograph. Additionally, other types of flow meters which are sensitive to both pressure and rate of air flow, as for example a hot wire anemometer, could be used in place of the pneumotachograph, but they would require additional electronic circuitry to compensate for errors introduced by virtue of sensitivity to the varying pressure.

The pneumotachograph 37 provides a resistance by means of a resistive device 35 which comprises a large number of ducts (0.8 mm in diameter by 32 mm in length). The resistance 35 creates a differential pressure signal between two spaced points in the driver tube 17. This differential pressure appears across the pneumotachograph output passages 39 and 41 and, in accordance with Poiseuille's Law, is proportional to the rate of air flow through the tube 17. The differential pressure is applied to a pressure transducer 40 which, for example, may be a differential pressure transducer manufactured by Validyne Corp. of Northridge, Calif. and sold as Model MP-45-14-871. Pressure transducer 40 converts the differential pressure to an analog voltage signal having an amplitude proportional to the applied differential pressure.

The analog voltage is input to an amplifier 38 and is then digitized by an analog-to-digital (A/D) interface circuit 45. Amplifier 38 and A/D interface 45 are well known circuit elements that are state-of-the art integrated circuits.

The A/D interface circuit 45, under the control of a microcomputer 44, which may be, for example, an Apple II Plus, samples the output signal from transducer 40 during systole or diastole. The transducer output is typically sampled and digitized to 12-bit accuracy every 1.025 milliseconds. The trigger signal for synchronizing the A/D interface circuit 45 to the onset of either systole or diastole is provided by a SYNC OUT signal from the control circuit 27 of the heart driver 20, as schematically represented by line 46. This signal provides appropriate pulses signaling the onset and termination of the systolic and diastolic phases, depending on whether the rate of air flow is to be measured during systole or diastole. During typical operation, 1200 samples are taken during each measurement cycle and stored as an array in the memory of microcomputer 44. Sampling terminates when a pulse, indicating the onset of the next phase, appears on the SYNC OUT line 46.

The microcomputer 44 is programmed in accordance with well known digital programming techniques to search the array of stored digital values to find the beginning and end of the sampled phase. The computer then consecutively sums the stored values lying between these beginning and end points to obtain a result corresponding to the integral of the rate of air flow during the measured systolic or diastolic phase. A calibration equation is employed to convert the integrated air flow to stroke volume expressed in milliliters. This stroke volume can then be multiplied by the ventricular rate to yield a ventricular blood flow figure in terms of volume of blood pumped per unit of time.

Figure 4A:
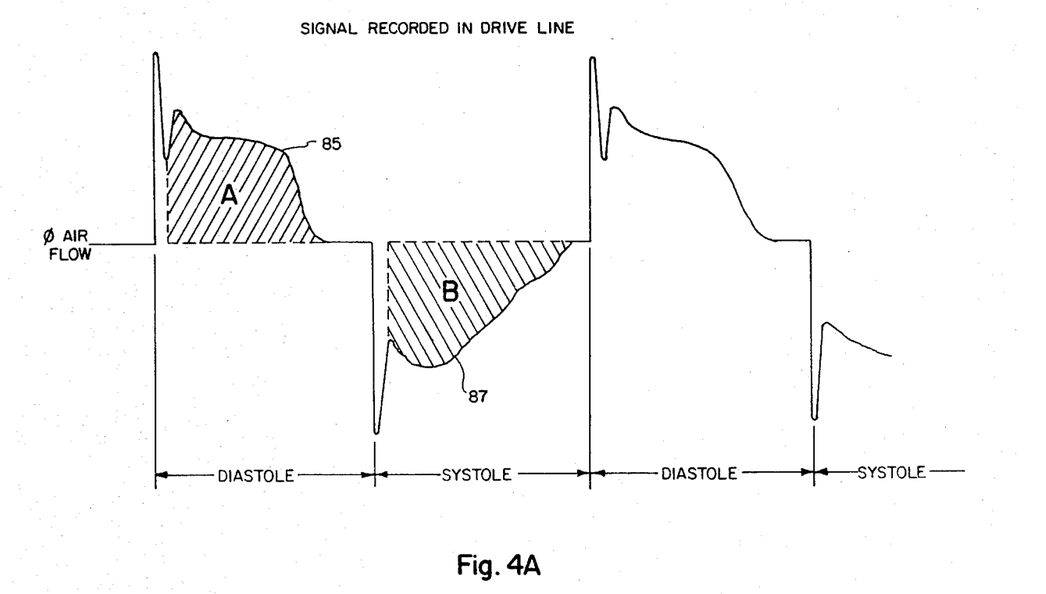
FIG. 4a is a plot of air flow versus time in a typical measurement made with the embodiment of FIG. 1.

The stroke volume and cardiac output values are displayed at the display terminal 43 of microcomputer 44. During this processing, sampling of the systolic or diastolic rate of air flow is suspended; sampling is resumed after the stroke volume and cardiac output values, which are computed from the previous samples, are displayed. Systolic or diastolic periods are sampled over approximately 30 seconds and the average results are graphically and numerically displayed as the average stroke volume and average cardiac output. A typical graph of the output (i.e. air flow versus time) is schematically illustrated in FIG. 4a. If the cardiac output is derived from integration of the air flow/time curve 85 during diastole, the area represented by the cross-hatched area A is used. Similarly, if the cardiac output is derived from integrating the air flow time/curve 87 during systole, the cross-hatched area B is used. In either case the cross-hatched area under the curve corresponds to within ±5–10% of the volume of blood pumped by the ventricle 10.

The form of the air flow/time curve 85, 87 recorded during diastole and systole contains important information of great diagnostic value concerning the operation of the inflow and outflow valves, and also concerning the hemodynamic state of the patient. Additionally, significant points on the air flow/time curve 85, 87 may be recognized by appropriate programming of the computer, which may be part of a sophisticated control system for the heart driver. For example, complete filling of the ventricle could result in zero air flow before the end of a pre-set diastolic length of time. Recognition of this complete filling could be used in a control system to terminate diastole and initiate the transition to systole.

Figure 2:
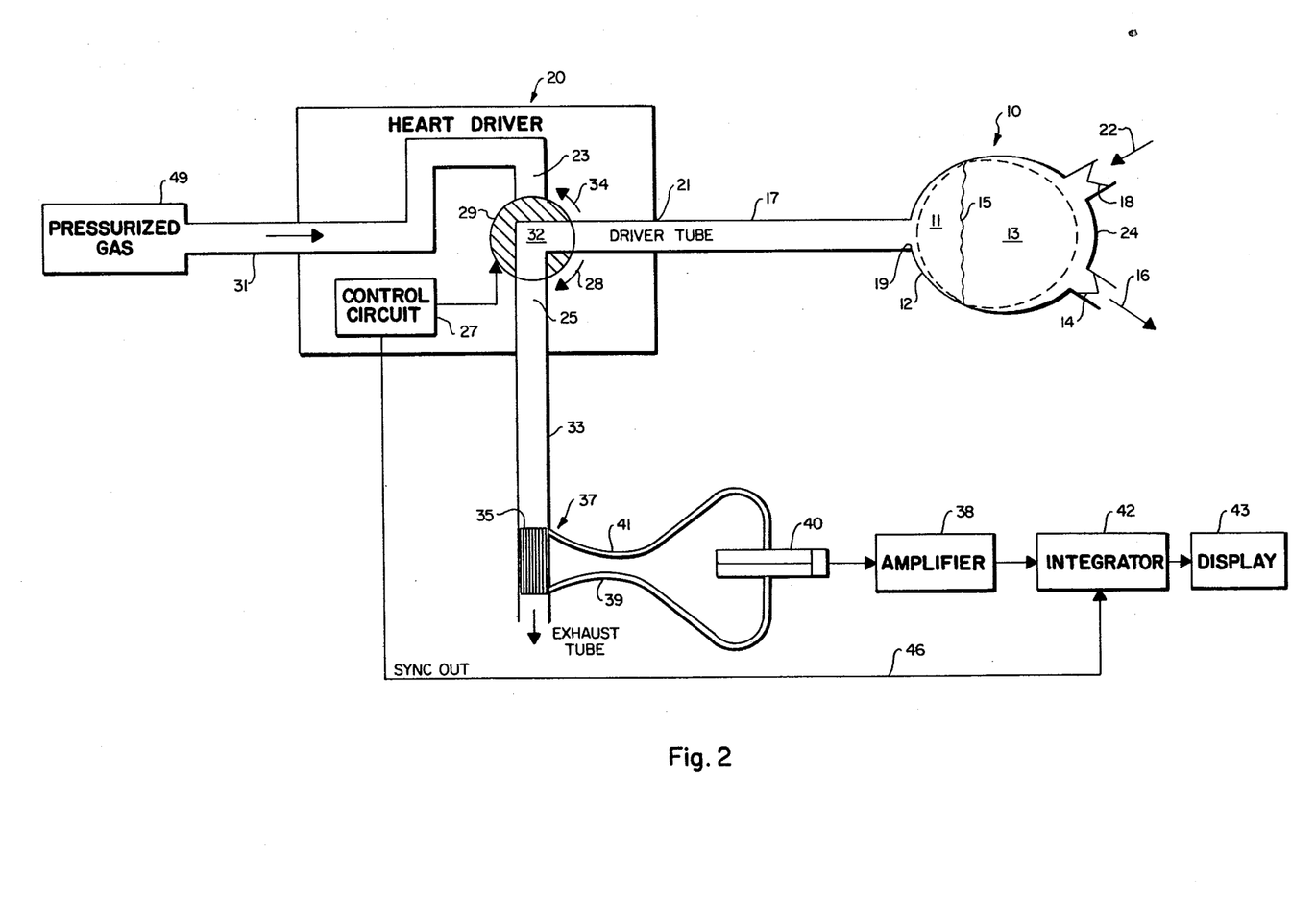
FIG. 2 is a schematic representation of an alternative system and method of the present invention wherein the ventricular blood flow measurements are derived from the rate of air flow from the artificial ventricle during diastole.

An alternative embodiment of the system and method of the present invention is schematically illustrated in FIG. 2. This embodiment differs only in that the flow meter 37 is placed in the flow path of the exhaust tube 33 rather than the driver tube 17, and the output of amplifier 38 is processed by an analog integrator 42 rather than by a digital computer. As more fully explained below, in this particular embodiment the cardiac flow measurements are derived solely from the rate of air flow exhausted during diastole.

At the onset of diastole, driver tube 17 and the gas chamber 11 contain air at end-systolic pressure, which pressure is usually on the order of 150 mm Hg above atmospheric pressure in the case of a left ventricle, and 70 mm Hg, in the case of the right ventricle. This gas rapidly escapes via driver tube 17 and exhaust port 25 and, as a consequence, the air pressure in the gas chamber 11 rapidly falls toward atmospheric pressure. When the gas pressure in chamber 11 falls below the aortic pressure, there is a reflux of blood from the aorta into the ventricle blood chamber 13. This causes the outflow valve 14 to close. When the pressure in gas chamber 11 falls below atrial pressure, the inflow valve 18 opens and blood begins to enter the ventricle. The volume of blood entering blood chamber 13 during diastole displaces a corresponding volume of gas from gas chamber 11, which gas is vented to atmosphere via the valve 29 and exhaust tube 33. The pressure of the gas in the exhaust tube 33 during diastole is essentially constant and close to atmospheric pressure.

Figure 4B:
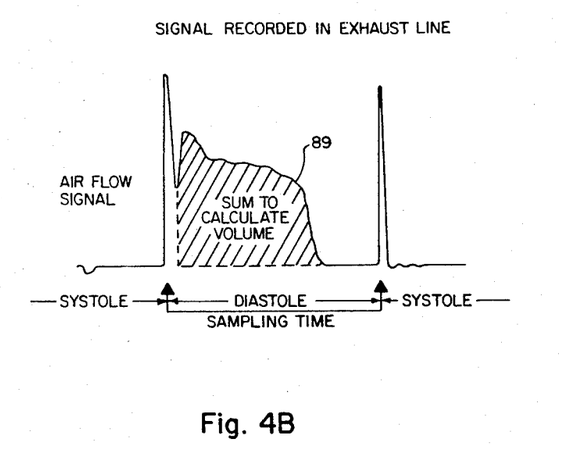
FIG. 4b is a plot of air flow versus time using the embodiments of FIGS. 2 or 3.

The measurement of the volume of blood entering the blood chamber 13 during diastole may be derived from measurements of the volume of gas exhausted over the same period of time. This measurement corresponds to the time integral of the flow rate of the exhausted gas. In a manner similar to the method described in the FIG. 1 embodiment, the volume of gas exhausted during diastole is obtained by using the flow meter 37 to obtain the rate of air flow through exhaust tube 33. This rate is converted by transducer 40 to a corresponding electric signal 89 (see FIG. 4b), which is then integrated over time. The integration can be done by means of a digital computer, as described in FIG. 1, or by means of a conventional analog integrator 42 as shown in FIG. 2.

In this embodiment, the pneumotachograph 37 and transducer 40, in conjunction with the integrator 42 and display 43, technically measure the cardiac "input" rather than the cardiac "output" because the volume measured is the volume which enters the ventricle during diastole. It should be noted that the cardiac input and output are not necessarily equal to each other during each diastolic phase because of backflow which occurs through the prosthetic heart valves 14, 18.

At the onset of diastole, some ejected blood returns to the ventricle, which causes outflow valve 14 to close. After the valve 14 is closed, there is still some leakage through the valve. This same situation occurs with the inflow valve 18 during systole. Therefore, throughout the cardiac cycle, some blood is refluxing counter to the normal direction of flow and the cardiac inflow exceeds cardiac output in proportion to the backflow.

There are two methods which have been used to calibrate the cardiac output measurement system. In the first method, the system is calibrated against the reading of a turbine flow meter in an artificial circulation path. The turbine flow meter responds only to forward flow and, therefore, measures true cardiac output. The calibration equation for the cardiac output measurement system is derived by plotting turbo-flow meter output against the number representing the integral of the diastolic air flow, in the manner explained above. The artificial circulation is permitted to run over a greater range of cardiac outputs than would be experienced in vivo. The equation of the line of best fit to the experimental points is obtained and the relevant constants are substituted into the computer program to provide a direct indication of volume, as illustrated in the computer listing provided in the appendix to this specification.

The second method of calibration exploits the potential of the pneumotachograph system for estimating prosthetic heart valve backflow under real operating conditions. In this method, the pneumotachograph is calibrated directly with known flow rates of ambient air and the constants relating volume flow rate to the A/D output are substituted into the computer program. Synchronization can be effected by the SYNC OUT signal on line 46 to assure that only exhaust flow, and not supply flow, is measured.

Figure 3:
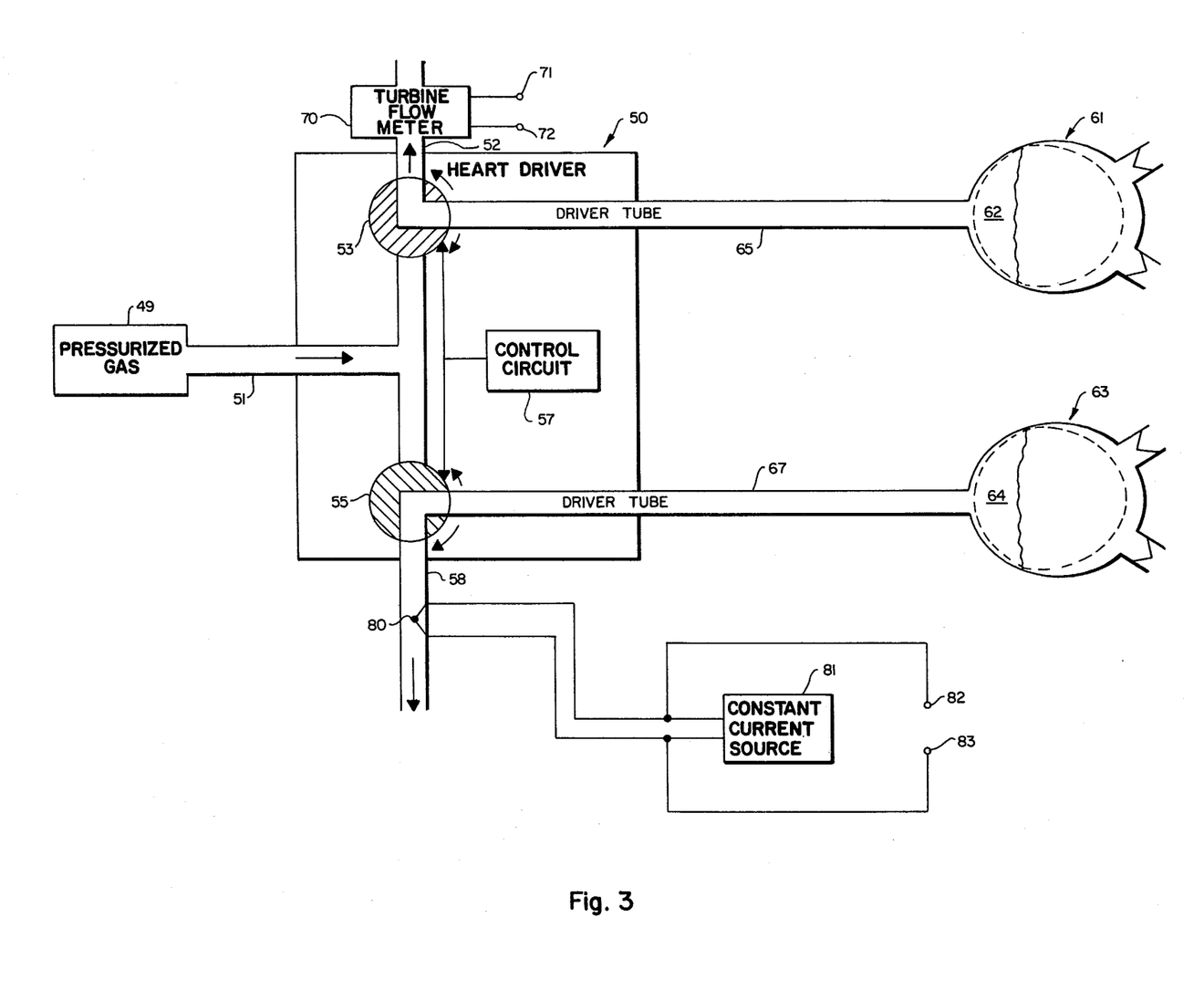
FIG. 3 is a schematic representation of a total artificial heart consisting of both a left and a right ventricle, and illustrating alternative ways of measuring the rate of air flow from the ventricles during diastole.

It will be appreciated that other techniques for measuring the rate of exhausted air flow can be employed. In addition, the principles of the present invention are adaptable for use with both ventricles of an artificial heart. A system illustrating these alternatives is shown in FIG. 3, to which specific reference is now made.

A source 49 of gas under pressure delivers pressurized gas through tube 51 to a heart driver unit 50. The heart driver may typically be the Utah Heart Driver referred to hereinabove, employed to serve two artificial ventricles 61, 63. Both ventricles 61, 63 are the same in their structure and operation as the ventricle 10 described earlier. Together, the two ventricles, one for the left side and one for the right side, constitute a total artificial heart.

Two electropneumatically controlled valves 53, 55 are operated under control of the electronic circuit 57 to alternately vary the flow connections of two driver tubes 65, 67 between inlet tube 51 during systole and exhaust tubes 52, 58 during diastole. Specifically, valve 53 alternately connects driver tube 65 to inlet tube 51 or to exhaust tube 52, whereas valve 55 alternately connects driver tube 67 to inlet tube 51 or to exhaust tube 58.

The driver tube 65 connects to the gas chamber 62 of ventricle 61, and the driver tube 67 connects to the gas chamber 64 of ventricle 63. Thus heart driver 50 operates in the same manner described in relation to the embodiment of FIG. 1 to periodically operate valves 53, 55 to effect systolic and diastolic phases of the ventricles 61, 63. During systole, there is pressurized gas applied to ventricle gas chambers 62, 64; during diastole, the gas is exhausted from these chambers via exhaust tubes 52, 58.

As explained above, during diastole the pressure of the exhausted air is essentially constant. Thus, even if a particular type of flow meter is sensitive to pressure changes, air flow measurements taken during diastole will not be adversely affected. For example, air flow through exhaust tube 52 is shown as being measured by a conventional turbine-type flow meter 70. In the alternative, a Doppler ultrasonic flow meter could be used. The turbine-type flow meter 70 is disposed in the flow path such that passing gas causes a propeller (not shown) to rotate at an angular speed which is proportional to the exhaust gas flow rate. A built-in tachometer (not shown) converts the angular speed of the propeller to a proportional voltage appearing across terminals 71, 72. Flow meter 70 could also be situated upstream of valve 53 rather than in the exhaust tube 52. From terminals 71, 72, the signal representing the rate of air flow may be processed and integrated either digitally as in FIG. 1, or by an analog integrator as in FIG. 2.

Another approach to measuring exhaust flow volume is shown in the exhaust passage downstream of valve 55. Specifically, a hot wire anemometer 80 is employed in the exhaust passage and takes the form of a wire, film or thermistor, which is held at a given temperature by a constant current source 81. As gas flows past the anemometer element 80, the element cools such that its electrical resistance is changed. Since the current through the element is held constant, the voltage across the element changes in proportion to the change in resistance. This voltage, as measured across terminals 82, 83, is a measure of the rate of air flow, which may be integrated as described above to yield measurements of volume.

While the invention has been described and illustrated by reference to specific embodiments, it will be clear that variations of the details of construction which are specifically illustrated and described may be resorted to without departing from the true spirit and scope of the invention as defined in the appended claims.

What we claim is:

1. A cardiac flow measurement system for measuring the volume of blood pumped over a specified period of time by a fluid driven artificial ventricle, said ventricle having a first chamber for receiving a drive fluid and a second chamber for receiving blood, said chambers being separated by a flexible diaphragm, and said system comprising:

first means for delivering a drive fluid to said first chamber;

second means through which the drive fluid is removed from said first chamber;

means for alternately (a) establishing a flow path between said first chamber and said first means so as to deliver said drive fluid to the first chamber at time-spaced intervals, and for alternately (b) establishing a flow path between said first chamber and said second means so as to remove the drive fluid from said first chamber at times in between said time-spaced intervals;

means, positioned in one of said flow paths between, for measuring the flow rate of said drive fluid independently of pressure variations which may occur in the flow path of the drive fluid; and means, connected to said measuring means, for integrating said flow rate over a specified time interval so as to derive the approximate cardiac output of said artificial ventricle during said specified time interval.

2. The system as defined in claim 1 wherein said means for measuring flow rate is positioned in the flow path established between said first chamber and said first means.

3. The system as defined in claim 1 wherein said means for measuring the flow rate of said drive fluid is positioned in the flow path established between said first chamber and said second means.

4. The system as defined in claims 2 or 3 wherein said means for measuring the flow rate of said drive fluid comprises means for establishing a differential pressure between two points in the flow path.

5. The system as defined in claim 4 wherein said means for integrating said flow rate over a specified time interval comprises:

means for converting the differential pressure into an electrical analog signal proportional in its amplitude to the differential pressure;

means for amplifying the electrical analog signal;

means, connected to the output of said amplifying means, for digitizing said signal; and means, connected to the output of said digitizing means, for digitally calculating the integral of said signal over a specified time interval.

6. The system as defined in claim 5 further comprising means for graphically displaying the said integrated signal.

7. The system as defined in claim 4 wherein said means for integrating said flow rate comprises:

means for converting said differential pressure to an electrical analog signal proportional in its amplitude to the differential pressure;

means for amplifying the analog signal; and means, connected to the output of said amplifying means, for integrating the analog signal.

8. The system as defined in claim 7 further comprising means for graphically displaying the said integrated signal.

9. The system as defined in claim 4 wherein said means for establishing the said differential pressure in said flow path comprises a pneumotachograph.

10. The system as defined in claim 3 wherein said means for measuring the flow rate of said drive fluid comprises a turbine flow meter.

11. The system as defined in claim 3 wherein said means for measuring the flow rate of said drive fluid comprises:

a heat sensitive element positioned in said flow path;

means connected to said heat sensitive element for passing a constant current through said element so as to maintain it at a constant temperature in said flow path; and means for sensing voltage variations across the heat sensitive element as the current which is passed through said element is either increased or decreased in order to maintain it at the said constant temperature.

12. The system as defined in claim 1 wherein said means for measuring the flow rate of said drive fluid is located outside the body of the patient.

13. A cardiac flow measurement system for measuring the volume of blood pumped over a specified period of time by a fluid/driven artificial ventricle, said ventricle having a first chamber for receiving a drive fluid and a second chamber for receiving blood, said chambers being separated by a flexible diaphragm, and said system comprising:

first means for delivering a drive fluid to said first chamber;

second means through which the drive fluid is removed from said first chamber;

means for alternately (a) establishing a flow path between said first chamber and said first means so as to deliver said drive fluid to the first chamber at time-spaced intervals, and for alternately (b) establishing a flow path between said first chamber and said second means so as to remove the drive fluid from said first chamber at times in between said time-spaced intervals;

means, positioned in the flow path established between said first chamber and said first means, for measuring the flow rate of said fluid through said flow path independently of pressure variations occurring in said flow path established between said first chamber and said first means;

means, connected to said means for measuring the flow rate, for converting the measured flow rate into an electrical analog signal proportional in its amplitude to the measured flow rate;

means for integrating the electrical analog signal over a specified time interval so as to derive therefrom the approximate cardiac output of said artificial ventricle during the specified time interval; and means for displaying the cardiac output derived from said integrating means.

14. A cardiac flow measurement system for measuring the volume of blood pumped over a specified period of time by a fluid driven artificial ventricle, said ventricle having a first chamber for receiving a drive fluid and a second chamber for receiving blood, said chambers being separated by a flexible diaphragm, and said system comprising:

first means for delivering a drive fluid to said first chamber;

second means through which the drive fluid is removed from said first chamber;

means for alternately (a) establishing a flow path between said first chamber and said first means so as to deliver said drive fluid to the first chamber at time-spaced intervals, and for alternately (b) establishing a flow path between said first chamber and said second means so as to remove the drive fluid from said first chamber at times in between said time-spaced intervals;

means, positioned in the flow path established between said first chamber and said second means, for measuring the flow rate of said drive fluid;

means, connected to said means for measuring the flow rate of said drive fluid, for converting the measured flow rate to an electrical analog signal proportional to the measured flow rate;

means for integrating the analog signal over a specified time interval so as to derive therefrom the approximate cardiac output of said artificial ventricle during said specified time interval; and means for displaying the cardiac output derived from said integrating means.

15. A method of measuring the volume of blood pumped over a specified period of time by a fluid driven artificial ventricle, said ventricle having a first chamber for receiving a drive fluid and a second chamber for receiving blood, said chambers being separated by a flexible diaphragm, and the method comprising the steps of:

delivering a drive fluid to said first chamber at time-spaced intervals;

removing the drive fluid from said first chamber at times in between the time-spaced intervals;

measuring the flow rate of said drive fluid independently of pressure variations which may occur in the flow path of the fluid; and integrating the measured flow rate over a specified time interval so as to derive therefrom the approximate cardiac output of said artificial ventricle during the specified time interval.

16. The method as defined in claim 15 wherein the step of measuring the flow rate of said drive fluid comprises the step of measuring said flow rate during the period of time that the drive fluid is delivered to said first chamber.

17. The method as defined in claim 15 wherein said step of measuring the flow rate of said drive fluid comprises the step of measuring the flow rate during the period of time that the drive fluid is removed from the first chamber.

18. The method as defined in claims 16 or 17 wherein said step of measuring the flow rate of said fluid comprises the step of establishing a differential pressure in a flow path through which the fluid is flowing.

19. The method as defined in claim 18 wherein said step of integrating the flow rate comprises the steps of:
converting the differential pressure to an electrical analog signal;
amplifying the electrical analog signal;
digitizing the amplified signal; and
digitally calculating the integral of said digitized signal.

20. The method as defined in claim 19 further comprising the step of graphically and numerically displaying the integrated signal.

21. The method as defined in claim 18 wherein said step of integrating the measured flow rate of said gas comprises the steps of:
converting the differential pressure to an electrical analog signal;
amplifying the analog signal; and
integrating the analog signal over the specified time interval.

22. The method as defined in claim 21 further comprising the step of graphically and numerically displaying the integrated signal.

23. The method as defined in claim 15 wherein said step of measuring the flow rate is done noninvasively.

24. A method of measuring the volume of blood pumped over a specified period of time by a fluid driven artificial ventricle, said ventricle having a first chamber for receiving a drive fluid and a second chamber for receiving blood, said chambers being separated by a flexible diaphragm, and the method comprising the steps of:

delivering a drive fluid to said first chamber at time-spaced intervals so as to cause the diaphragm to expel blood from the second chamber during the said intervals;

removing the drive fluid from said first chamber at times in between the said time-spaced intervals to permit blood to re-enter the second chamber;

measuring the flow rate of said fluid independently of pressure variations occurring in the fluid's flow path during the time that the fluid is being delivered to said first chamber;

converting the measured flow rate to an electrical analog signal;

integrating the electrical analog signal over a specified time interval so as to derive therefrom the approximate cardiac output of said artificial ventricle during the specified time interval; and displaying the integrated signal.

25. A method of measuring the volume of blood pumped over a specified period of time by a fluid/-driven artificial ventricle, said ventricle having a first chamber for receiving a drive fluid and a second chamber for receiving blood, said chambers being separated by a flexible diaphragm, and the method comprising the steps of:

delivering a drive fluid to said first chamber at time-spaced intervals so as to cause the diaphragm to expel blood from the second chamber during said intervals;

removing the drive fluid from said first chamber at times in between said time-spaced intervals to permit blood to re-enter the second chamber;

measuring the flow rate of said fluid during the time the fluid is removed from said first chamber;

converting the measured flow rate to an electrical analog signal;

integrating the electrical analog signal over a specified time interval so as to derive therefrom the approximate cardiac output of said artificial ventricle during said specified time interval; and displaying the integrated signal.

26. A cardiac flow measurement system for measuring the volume of blood pumped over a specified period of time by an artificial ventricle, said ventricle having a first chamber for receiving a fluid and a second chamber for receiving blood, said chambers being separated by a flexible diaphragm, and said system comprising:

first means for delivering the fluid to said first chamber during specified time intervals corresponding to systole;

second means through which the fluid is removed from said first chamber at specified time intervals corresponding to diastole;

means for imparting a pumping action to said diaphragm so as to alternately expel blood from said second chamber during the time interval corresponding to systole and so as to permit re-entry of blood into the second chamber during the time interval corresponding to diastole;

means for measuring the flow rate of said fluid independently of pressure variations which may occur in the flow path of the fluid; and means for integrating said flow rate over one of said specified systolic or diastolic time intervals so as to derive the approximate cardiac output of said artificial ventricle.

27. The method of measuring the volume of blood pumped over a specified period of time by an artificial ventricle, said ventricle having a first chamber for receiving a fluid and a second chamber for receiving blood to be pumped by the ventricle, said chambers being separated by a flexible diaphragm, and the method comprising the steps of:

delivering fluid to said first chamber at time-spaced intervals corresponding to systole;

removing the fluid from said first chamber at time-spaced intervals corresponding to diastole;

measuring the flow rate of said fluid independently of pressure variations which may occur in the flow path of the fluid; and integrating the measured flow rate over one of said diastolic or systolic time intervals so as to derive therefrom the approximate cardiac output of said artificial ventricle.

* * * * *

UNITED STATES PATENT AND TRADEMARK OFFICE
CERTIFICATE OF CORRECTION

PATENT NO. : 4,465,063
DATED : August 14, 1984
INVENTOR(S) : Nielsen et al.

It is certified that error appears in the above-identified patent and that said Letters Patent is hereby corrected as shown below:

Column 11, line 25, delete "between".

Signed and Sealed this

Twenty-sixth Day of February 1985

[SEAL]

Attest:

DONALD J. QUIGG

Attesting Officer     Acting Commissioner of Patents and Trademarks